(12) United States Patent
Kim

(10) Patent No.: US 9,220,482 B2
(45) Date of Patent: Dec. 29, 2015

(54) METHOD FOR PROVIDING ULTRASOUND IMAGES AND ULTRASOUND APPARATUS

(71) Applicant: SAMSUNG MEDISON CO., LTD., Gangwon-do (KR)

(72) Inventor: Nam-Woong Kim, Gangwon-do (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 0 days.

(21) Appl. No.: 13/682,192

(22) Filed: Nov. 20, 2012

(65) Prior Publication Data
US 2013/0237824 A1 Sep. 12, 2013

(30) Foreign Application Priority Data
Mar. 9, 2012 (KR) .................. 10-2012-0024505

(51) Int. Cl.
A61B 8/00 (2006.01)
A61B 8/08 (2006.01)
A61B 8/13 (2006.01)
(Continued)

(52) U.S. Cl.
CPC . *A61B 8/523* (2013.01); *A61B 8/13* (2013.01); *A61B 8/4254* (2013.01); *A61B 8/4444* (2013.01); *A61B 8/463* (2013.01); *A61B 8/466* (2013.01); *A61B 8/483* (2013.01); *G01S 7/5205* (2013.01); *G01S 7/52063* (2013.01); *G01S 7/52073* (2013.01); *G01S 7/52074* (2013.01); *A61B 8/0866* (2013.01); *G01S 15/8993* (2013.01)

(58) Field of Classification Search
CPC ............ A61B 8/483; A61B 8/14; A61B 8/00; A61B 8/463; A61B 8/13; A61B 8/523; A61B 8/0866; A61B 8/4254; A61B 8/466; G01S 15/8993; G01S 7/52073; G01S 7/5205; G01S 7/52063; G01S 7/52074; G06T 2219/008
USPC .................................................. 600/437–469
See application file for complete search history.

(56) References Cited

U.S. PATENT DOCUMENTS 6,290,648 B1 9/2001 Kamiyama
7,798,966 B2 * 9/2010 Kawashima et al. ......... 600/443
(Continued)

FOREIGN PATENT DOCUMENTS

DE 102 58 952 A1 8/2004
EP 1 504 721 A1 2/2005
(Continued)

OTHER PUBLICATIONS

Extended European Search Report issued in European Patent Application No. EP 13156316.5 dated May 6, 2013.
(Continued)

*Primary Examiner* — Sanjay Cattungal
(74) *Attorney, Agent, or Firm* — McDermott Will & Emery LLP

(57) ABSTRACT

A method of providing an ultrasound image, the method including: marking a cut line or a cut surface on a 3-dimensional (3D) ultrasound image of an object which is obtained by using a probe, wherein the cut line and the cut surface are used to view a cross section of the 3D ultrasound image; detecting motion information about the probe by using a sensor included in the probe; and changing a location of the cut line or the cut surface based on the detected motion information about the probe.

13 Claims, 5 Drawing Sheets

(51) Int. Cl.
*G01S 7/52* (2006.01)
*G01S 15/89* (2006.01)

(56) References Cited

U.S. PATENT DOCUMENTS

| | | | |
|---|---|---|---|
| 8,103,066 B2* | 1/2012 | Kim et al. | 382/128 |
| 2005/0090743 A1* | 4/2005 | Kawashima et al. | 600/443 |
| 2007/0073148 A1* | 3/2007 | Kim | 600/437 |
| 2007/0276247 A1 | 11/2007 | Chalana et al. | |
| 2008/0009727 A1* | 1/2008 | Kataguchi | 600/437 |
| 2008/0132788 A1* | 6/2008 | Schreckenberg et al. | 600/443 |
| 2008/0146932 A1 | 6/2008 | Chalana et al. | |
| 2009/0082668 A1* | 3/2009 | Hamada et al. | 600/443 |
| 2009/0209859 A1* | 8/2009 | Tsujita et al. | 600/445 |
| 2010/0174192 A1* | 7/2010 | Azuma | 600/443 |
| 2011/0066031 A1* | 3/2011 | Lee et al. | 600/443 |
| 2011/0144499 A1* | 6/2011 | Yoo et al. | 600/443 |
| 2011/0306025 A1* | 12/2011 | Sheehan et al. | 434/267 |
| 2012/0262453 A1* | 10/2012 | Endo et al. | 345/419 |
| 2012/0289833 A1* | 11/2012 | Kashima et al. | 600/445 |
| 2014/0152661 A1* | 6/2014 | Nishiura | 345/424 |

FOREIGN PATENT DOCUMENTS

| | | |
|---|---|---|
| EP | 1 847 222 A1 | 10/2007 |
| EP | 2 491 865 A1 | 8/2012 |
| JP | 2000-107185 A | 4/2000 |
| JP | 2010-051817 A | 3/2010 |
| KR | 10-2007-0031027 A | 3/2007 |
| KR | 10-2008-0001059 A | 1/2008 |

OTHER PUBLICATIONS

Korean Office Action, w/ English translation thereof, issued in Korean Patent Application No. 10-2012-0024505 on Jul. 1, 2013.
Korean Notice of Allowance issued in Korean Application No. 10-2012-0024505 with Date of mailing Jan. 17, 2014, with English Translation.

* cited by examiner

FIG. 4
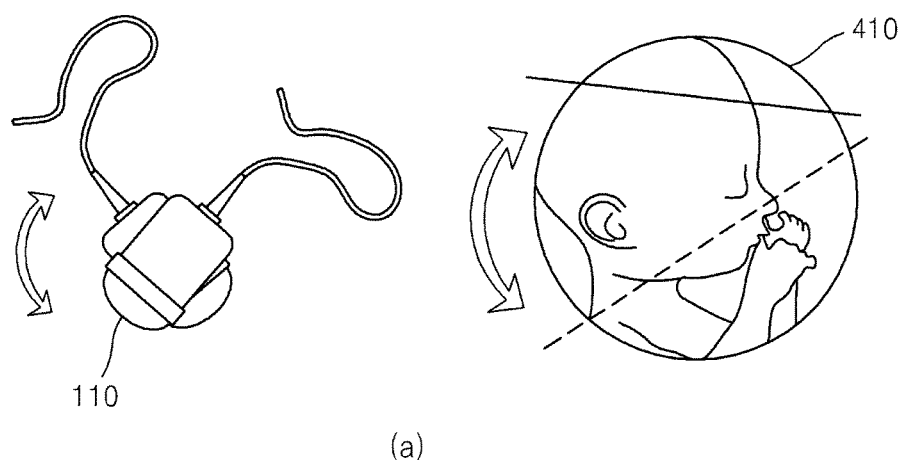
(a)
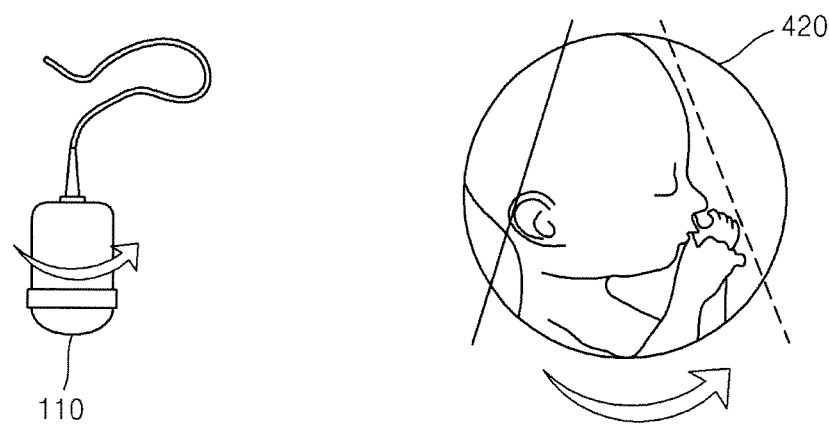
(b)

METHOD FOR PROVIDING ULTRASOUND IMAGES AND ULTRASOUND APPARATUS

CROSS-REFERENCE TO RELATED PATENT APPLICATION

This application claims the benefit of Korean Patent Application No. 10-2012-0024505, filed on Mar. 9, 2012, in the Korean Intellectual Property Office, the disclosure of which is incorporated herein in its entirety by reference.

BACKGROUND OF THE INVENTION

1. Field of the Invention

The present invention relates to a method and apparatus for providing ultrasound images that a user wants to view by using a probe including a sensor.

2. Description of the Related Art

Ultrasound diagnosis apparatuses transmit ultrasound signals from a surface of a human body to be diagnosed toward a part in vivo and obtain images related to a cross-section of soft tissue or blood flow by using information regarding ultrasound signals reflected from the part.

Ultrasound diagnosis apparatuses have various advantages, including a compact size, low cost, and real-time display. Also, ultrasound diagnosis apparatuses have excellent stability because there is no fear of X-ray exposure, and thus, the ultrasound diagnosis apparatuses are commonly used together with other diagnosis apparatuses, such as computerized tomography (CT) scanners, magnetic resonance imaging (MRI) apparatuses, nuclear medicine diagnosis apparatuses, or the like.

However, it is difficult for a user to obtain a 2-dimensional ultrasound image that he or she wants to view at once by using an ultrasound diagnosis apparatus. This is because various 2-dimensional ultrasound images may be obtained according to the location of a probe or an angle between the probe and a subject to be diagnosed.

Also, when a typical ultrasound diagnosis apparatus is used, a user manipulates a probe by using one of his or her hands and manipulates a control panel of the ultrasound diagnosis apparatus by using the other hand to obtain an ultrasound image, and the obtained ultrasound image is displayed on a display unit. Also, the user manipulates a track ball and various buttons of the control panel to rotate the displayed ultrasound image in a particular orientation or at a particular angle. In this regard, if the obtained ultrasound image is not what the user wants to view, the user places the probe on the subject to be diagnosed and then obtains a new ultrasound image. However, it is difficult for the user to remember the location of the probe and the angle between the probe and the subject to be diagnosed which were used when the previous ultrasound image was obtained.

Accordingly, there is a need for a system that allows a user to easily obtain a 2-dimensional ultrasound image that he or she wants to view by using an ultrasound diagnosis apparatus.

SUMMARY OF THE INVENTION

The present invention provides a method and apparatus for providing ultrasound images that a user wants to view by controlling the location of a cut line or a cut surface on a three-dimensional image by using a sensor included in a probe.

According to an aspect of the present invention, there is provided a method of providing an ultrasound image, the method including: marking a cut line or a cut surface on a 3-dimensional (3D) ultrasound image of an object which is obtained by using a probe, wherein the cut line and the cut surface are used to view a cross section of the 3D ultrasound image; detecting motion information about the probe by using a sensor included in the probe; and changing a location of the cut line or the cut surface based on the detected motion information about the probe.

The method may further include displaying a 2 dimensional (2D) ultrasound image corresponding to the changed location of the cut line or the cut surface.

The method may further include capturing the 2D ultrasound image on display.

The method may include: receiving a mode conversion command for converting a 3D image mode into a 2D image mode; and displaying a 2D ultrasound image corresponding to a location of the probe based on the mode conversion command in real time.

The receiving of the mode conversion command may include receiving the mode conversion command through a button included in the probe.

The displaying of the 2D ultrasound image in real time may further include: displaying the 2D ultrasound image corresponding to the location of the probe on a first region; and displaying on a second region a 3D ultrasound image on which a location corresponding to the 2D ultrasound image displayed on the first region is marked.

The motion information may include information about at least one selected from a tilting direction, tilting angle, rotational direction, and rotational angle of the probe.

The sensor may include at least one selected from a tilt sensor, a gyro sensor, a 3-axis magnetic sensor, and an acceleration sensor.

According to another aspect of the present invention, there is provided a ultrasound apparatus including: a probe including a sensor for detecting motion information; a display unit for marking a cut line or a cut surface on a 3D ultrasound image of an object which is obtained by using the probe to view a cross section of the 3D ultrasound image; an image processor for changing a location of the cut line or the cut surface, based on motion information of the probe detected by using the sensor; and a controller for controlling the probe, the display unit, and the image processor.

BRIEF DESCRIPTION OF THE DRAWINGS

The above and other features and advantages of the present invention will become more apparent by describing in detail exemplary embodiments thereof with reference to the attached drawings in which:

FIG. 4 is a diagram for explaining a method of controlling the location of a cut line or a cut surface by using a sensor of a probe, according to an embodiment of the present invention;

DETAILED DESCRIPTION OF THE INVENTION

Figure 1:
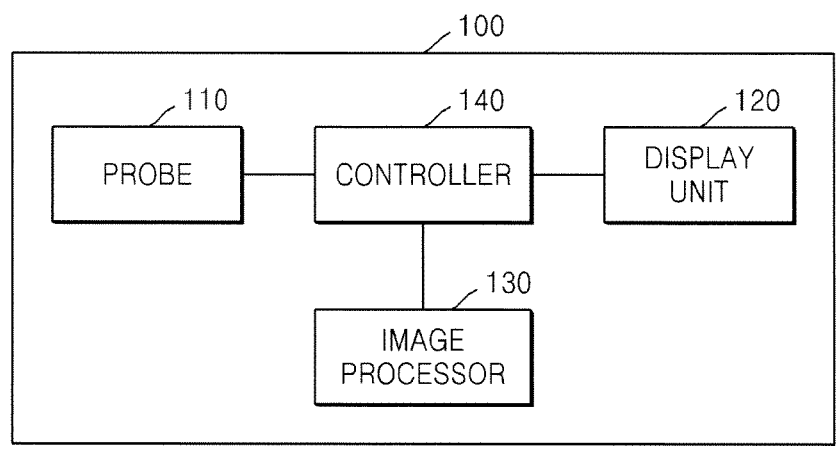
FIG. 1 is a block diagram of a structure of an ultrasound apparatus according to an embodiment of the present invention.

Expressions such as "at least one of," when preceding a list of elements, modify the entire list of elements and do not modify the individual elements of the list.

Most of the terms used herein are general terms that have been widely used in the technical art to which the present invention pertains. However, some of the terms used herein may be created to reflect the intentions of technicians in this art, precedents, or new technologies. Also, some of the terms used herein may be arbitrarily chosen by the present applicant. In this case, these terms are defined in detail below. Accordingly, the specific terms used herein should be understood based on the unique meanings thereof and the whole context of the present invention.

In the present specification, it should be understood that the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added. Also, the terms, such as 'unit' or 'module', etc., should be understood as a unit that processes at least one function or operation and that may be embodied in a hardware manner, a software manner, or a combination of the hardware manner and the software manner.

Throughout the specification, the term "ultrasound image" refers to an image of an object obtained by using an ultrasound. The term 'object' may be understood to be a part of a human body. For example, the object may be an organ, such as the liver, the heart, or the womb, or a fetus.

Throughout the specification, the term 'user' may be a medical professional, e.g., a doctor, a nurse, a clinical pathologist, or a medical imaging professional, but is not limited thereto.

In the following detailed description, only certain exemplary embodiments of the present invention have been shown and described, simply by way of illustration. As those of ordinary skill in the art would realize, the described embodiments may be modified in various different ways, all without departing from the spirit or scope of the present invention. Accordingly, the drawings and description are to be regarded as being illustrative in nature and not restrictive. Also, in the drawings, elements that are not related to the description are not illustrated to clearly describe the present invention, and throughout the specification, like elements are denoted by like reference numerals.

FIG. 1 is a block diagram of a structure of an ultrasound apparatus 100 according to an embodiment of the present invention.

The ultrasound apparatus 100 according to the present embodiment of the present invention refers to a device that obtains an ultrasound image of an object by using ultrasound, and displays the obtained ultrasound image to a user. An ultrasound image according to an embodiment of the present invention may be an image that is generated in at least one mode selected from a brightness mode (B mode), a color mode (C mode), a motion mode (M mode), a pulsed-wave (PW) mode, a continuous wave (CW) mode, a two-dimensional (2D) mode, and a three-dimensional (3D) mode.

The ultrasound apparatus 100 may be embodied in various forms. For example, the ultrasound apparatus 100 described in the present specification may be implemented in a mobile terminal as well as a fixable terminal. Examples of the mobile terminal may include a laptop computer, a personal digital assistant (PDA), a tablet personal computer (PC), and the like.

According to an embodiment of the present invention, the ultrasound apparatus 100 may include a probe 110, a display unit 120, an image processor 130, and a controller 140. However, the elements of FIG. 1 are not indispensable elements. The ultrasound apparatus 100 may include a greater number of elements or a lesser number of elements.

The probe 110 may transmit an (the?) ultrasound signal to an object, and may receive an ultrasound echo signal from the object. The probe 110 may be at least one selected from 1D (dimension), 1.5D, 2D (matrix), and 3D probes. The probe 110 according to an embodiment of the present invention is described below in detail with reference to FIG. 2.

The display unit 120 may display and output information processed by the ultrasound apparatus 100. For example, the display unit 120 may display a 3D ultrasound image of the object. The 3D ultrasound image according to an embodiment of the present invention may be formed based on volume data.

The volume data refers to a data set based on voxels that are consecutive 2D slices. In this regard, like a pixel that is a unit of a 2D image, a voxel is a unit of a 3D image, and has a density value.

According to an embodiment of the present invention, the display unit 120 may display on a 3D ultrasound image a cut line or cut surface which are used to view a 2D cross-section of the 3D ultrasound image in an oblique mode. In this regard, the display unit 120 may also display a 2D ultrasound image corresponding to the cut line or the cut surface. A 2D ultrasound image corresponding to the cut line or the cut surface according to an embodiment of the present invention may vary in real time according to the location of the cut line or the cut surface.

Also, the 2D ultrasound image corresponding to the cut line or the cut surface may be displayed together with the 3D ultrasound image. In this regard, in a 3D image mode, the 3D ultrasound image may be displayed in a larger region than the 2D ultrasound image.

The display unit 120 may display a captured 2D ultrasound image. If there are a plurality of captured images, the display unit 120 may display the captured images on a single screen.

According to an embodiment of the present invention, when a mode conversion command for converting a 3D image mode into a 2D image mode is received, the display unit 120 may display a 2D ultrasound image corresponding to the cut line or the cut surface in a 2D image mode. That is, the display unit 120 may display a 2D ultrasound image corresponding to the location of the probe 100 in real time based on the mode conversion command. In this regard, the display unit 120 may enlarge the 2D ultrasound image displayed in the 3D image mode and may display the enlarged image in the 2D image mode.

Also, the display unit 120 may display, in the 2D image mode, a 2D ultrasound image on a first region, and a 3D ultrasound image on which a location corresponding to the 2-dimensional ultrasound image displayed on the first region is marked on a second region. According to an embodiment of the present invention, the first region may be wider than the second region.

When the display unit 120 and a touch pad constitute a layer structure and thus form a touch screen, the display unit 120 may be used as an input apparatus as well as an output apparatus. The display unit 120 may include at least one selected from a liquid crystal display (LCD), a thin film transistor-liquid crystal display (TFT-LCD), an organic light-emitting diode (OLED), a flexible display, and a 3D display.

The image processor 130 may generate a 2D ultrasound image or 3D ultrasound image of an object by using ultrasound echo signals obtained by using the probe 110. Also, the image processor 130 may change the location of the cut line or cut surface marked on the 3D ultrasound image based on motion information about the probe 110 detected by a sensor.

The controller 140 may control the probe 110, the display unit 120, and the image processor 130. The controller 140 may capture a 2D ultrasound image corresponding to the cut line or cut surface based on an input of a user.

Also, the controller 140 may execute various modes. For example, the controller 140 may execute a 2D image mode, a 3D image mode, an oblique mode, or the like. A 2D image mode is a mode in which a 2D ultrasound image of an object is displayed. A 3D image mode is a mode in which volume data about the object is obtained and a corresponding 3D ultrasound image is displayed based on the obtained volume data. An oblique mode is a mode for displaying an image of an oblique cross-section obtained by cutting an arbitrary location of a 3D ultrasound image.

Also, the controller 140 may receive a mode conversion command, and may convert a mode that is currently executed in the ultrasound apparatus 100. For example, the controller 140 may receive a command for converting a 3D image mode into a 2D image mode and may convert the 3D image mode into the 2D image mode.

Figure 2:
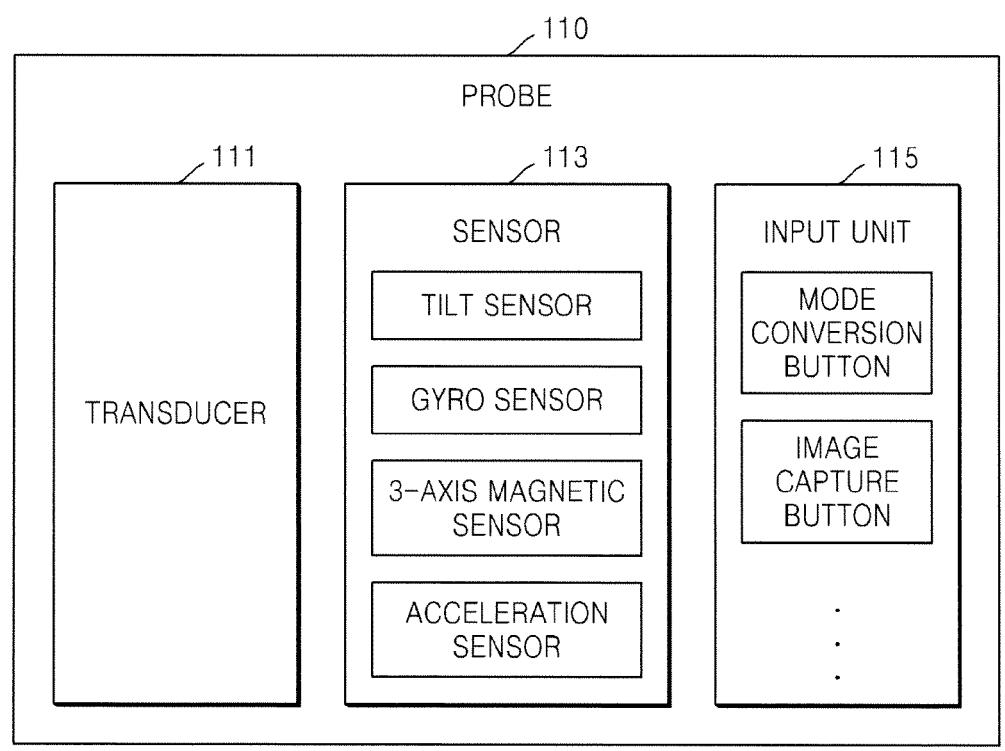
FIG. 2 is a block diagram of a structure of a probe according to an embodiment of the present invention.

FIG. 2 is a block diagram of a structure of the probe 100 according to an embodiment of the present invention.

Referring to FIG. 2, the probe 110 may include a transducer 111, a sensor 113, and an input unit 115. However, the elements of FIG. 2 are not indispensable. The probe 110 may include a greater number of elements or a lesser number of elements.

The transducer 111 may transmit ultrasound signals to an object. Also, the transducer 111 may receive ultrasound echo signals from the object.

The sensor 113 may detect motion information about the probe 110. The sensor 113 according to an embodiment of the present invention may be a tilt sensor, a gyro sensor, a 3-axis magnetic sensor, an acceleration sensor, or the like.

The motion information about the probe 110 according to an embodiment of the present invention refers to information about a degree of motion of the probe 110 in a 3D space. According to an embodiment of the present invention, the sensor 113 may have a reference location of the probe 110 which has been set in advance. Accordingly, when the probe 110 moves, the sensor 113 may compare the reference location of the probe 110 with a current location thereof and thus detect the motion information.

The motion information about the probe 110 according to an embodiment of the present invention may include information about at least one selected from a tilting direction, a tilting angle, a rotational direction, and a rotational angle of the probe 110.

Also, the sensor 113 may be located inside or outside the probe 110.

The input unit 115 may generate input data for controlling an operation of the ultrasound apparatus 100 by a user, and may be, for example, a user interface. According to an embodiment of the present invention, the input unit 115 may be located in a button shape on a surface of the probe 110.

The input unit 115 according to an embodiment of the present invention may include a mode conversion button for executing a mode conversion command between a 2D image mode and a 3D image mode, an image capture button for capturing a displayed image, or the like.

Hereinafter, a method of providing an ultrasound image by using the respective constituents of the ultrasound apparatus 100, in particular, the probe 110 of the ultrasound apparatus 100 is described in detail below with reference to FIGS. 3 and 5.

Figure 3:
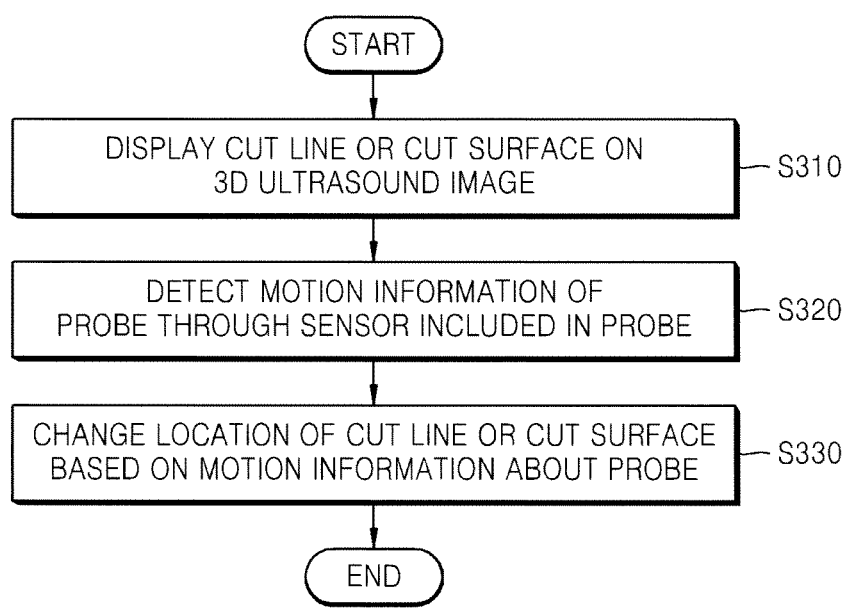
FIG. 3 is a flowchart of a method of providing an ultrasound image, according to an embodiment of the present invention.

Referring to FIG. 3, a method of providing an ultrasound image according to an embodiment of the present invention includes operations which are processed in time series by the ultrasound apparatus 100 of in FIGS. 1 and 2. Accordingly, even when not described below, if presented with reference to the ultrasound apparatus 100 of FIGS. 1 and 2, the description may also apply to the method of providing an ultrasound image described with reference to FIG. 3.

FIG. 3 is a flowchart of a method of providing an ultrasound image, according to an embodiment of the present invention.

The ultrasound apparatus 100 may mark a cut line or cut surface on a 3D ultrasound image obtained through the probe 110 (Operation 310). The cut line or the cut surface according to an embodiment of the present invention is used to view an oblique cross-sectional image of the 3D ultrasound image.

The ultrasound apparatus 100 may detect motion information about the probe 110 through the sensor 113 included in the probe 110 (Operation 320). The motion information about the probe 110 according to an embodiment of the present invention may include information about at least one selected from a tilting direction, tilting angle, rotational direction, and rotational angle of the probe 110.

For example, when a user tilts the probe 110 forward, the sensor 113 may detect a degree of the forward tilting of the probe 110, and may transmit this motion information to the controller 140 or the image processor 130.

Also, when a user rotates the probe 110 in a clockwise direction, the sensor 113 may detect the rotational angle (for example, 30)° and the rotational direction (clockwise direction), and may transmit the motion information to the controller 140 or the image processor 130.

Based on the motion information about the probe 110, the ultrasound apparatus 100 may change the location of the cut line or the cut surface (Operation 330). This changing process is described below in detail with reference to FIG. 4.

For example, as illustrated in FIG. 4A, when a user moves the probe 110 vertically, the ultrasound apparatus 100 may detect the vertical motion of the probe 110 through the sensor 113 included in the probe 110. Accordingly, the ultrasound apparatus 100 may move vertically a cut line or a cut surface marked on a 3D ultrasound image 410.

Also, as illustrated in FIG. 4B, when a user tilts or rotates the probe 110 laterally, the ultrasound apparatus 100 may detect the lateral motion of the probe 110 through the sensor 113 included in the probe 110. Accordingly, the ultrasound apparatus 100 may move laterally a cut line or a cut surface marked on a 3D ultrasound image 420.

That is, according to an embodiment of the present invention, a user may obtain an ultrasound image by using the probe 110 and may display the ultrasound image, and then, without manipulating a control panel, the user may control a cut line or cut surface on a 3D ultrasound image by moving the probe 110.

Figure 5:
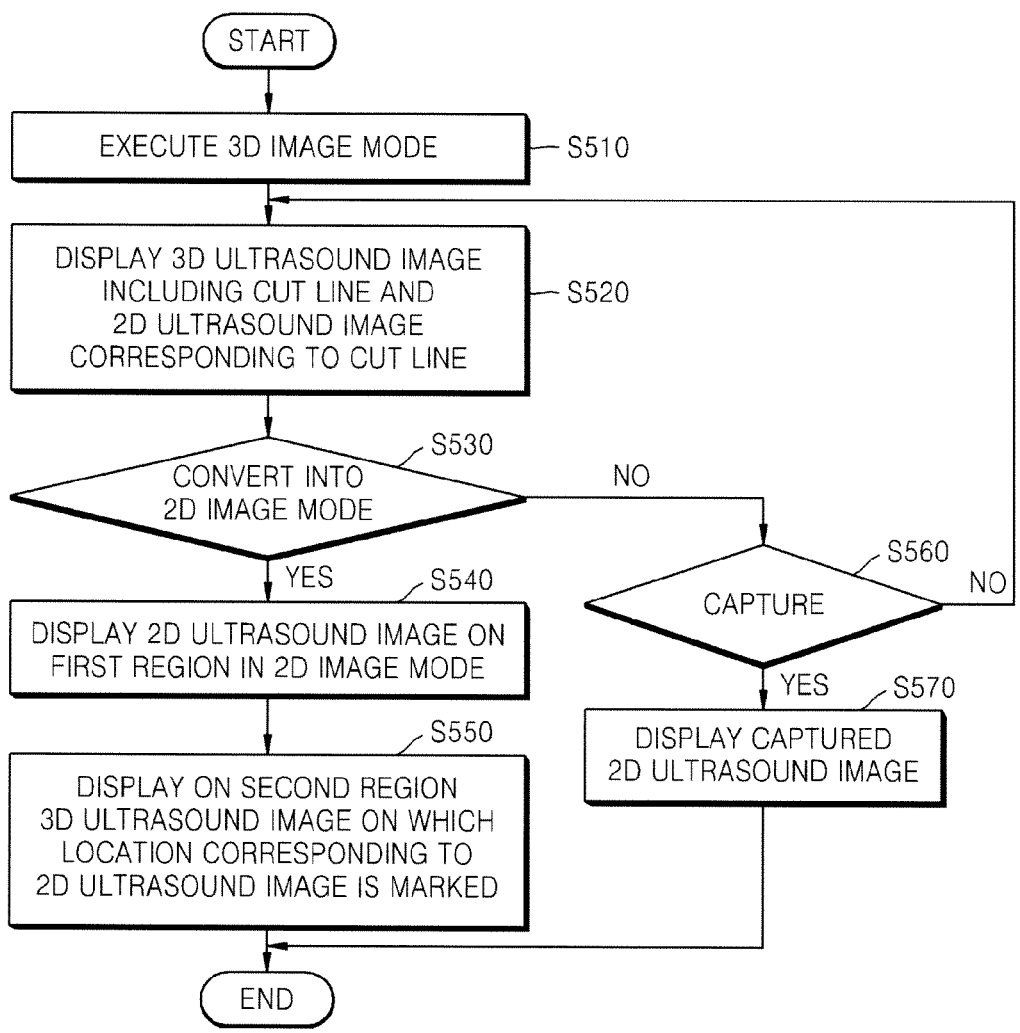
FIG. 5 is a flowchart of a method of providing an ultrasound image, according to another embodiment of the present invention.

FIG. 5 is a flowchart of a method of providing an ultrasound image, according to another embodiment of the present invention. Referring to FIG. 5, a method of providing an ultrasound image according to an embodiment of the present invention includes operations which are processed in time series in the ultrasound apparatus 100 of in FIGS. 1 and 2.

Accordingly, even when not described below, if presented with reference to the ultrasound apparatus 100 of FIGS. 1 and 2, the description may also apply to the method of providing an ultrasound image described with reference to FIG. 5.

According to an embodiment of the present invention, the ultrasound apparatus 100 may execute a 3D image mode (Operation 510). In this regard, the ultrasound apparatus 100 may obtain a 3D ultrasound image and may display the 3D ultrasound image together with a cut line or a cut surface. Also, the ultrasound apparatus 100 may display a 2D ultrasound image corresponding to the cut line or the cut surface (Operation 520).

A user may change the location of the cut line or the cut surface by tilting or rotating the probe 110 vertically or laterally. In this regard, according to motion information about the probe 110, a 2D ultrasound image on display may change in real time.

A user may identify a 2D ultrasound image which changes according to the change in the location of the cut line or cut surface. As soon as a 2D ultrasound image the user wants to view is displayed, the user fixes the location of the probe 110, and then inputs a command for conversion into a 2D image mode. In this regard, the ultrasound apparatus 100 may convert a 3D image mode into a 2D image mode based on the 2D image mode conversion command (Operation 530). By doing so, the user may easily determine a location of the probe 110 which is appropriate for obtaining a 2D ultrasound image the user wants to view.

According to an embodiment of the present invention, the mode conversion command may be input by using either a button included in the probe 110 or a control panel of the ultrasound apparatus 100.

According to an embodiment of the present invention, the ultrasound apparatus 100 may, in the 2D image mode, display a 2D ultrasound image on the first region (Operation 540). Also, the ultrasound apparatus 100 may display on the second region a 3D ultrasound image on which a location corresponding to the 2D ultrasound image is marked (Operation 550). The 3D ultrasound image on which a location corresponding to the 2D ultrasound image is marked according to an embodiment of the present invention may be displayed as an icon.

According to an embodiment of the present invention, the ultrasound apparatus 100 may receive a capture command with respect to a 2D ultrasound image (Operation 560). According to an embodiment of the present invention, a user may input a capture command by using either a button included in the probe 110 or a control panel of the ultrasound apparatus 100.

In this regard, the ultrasound apparatus 100 may capture a 2D ultrasound image on display and may display the captured image (Operation 570). According to an embodiment of the present invention, the ultrasound apparatus 100 may capture a plurality of 2D ultrasound images. That is, a user may capture a plurality of 2D ultrasound images obtained by changing the location of the cut line or the cut surface.

Figure 6:
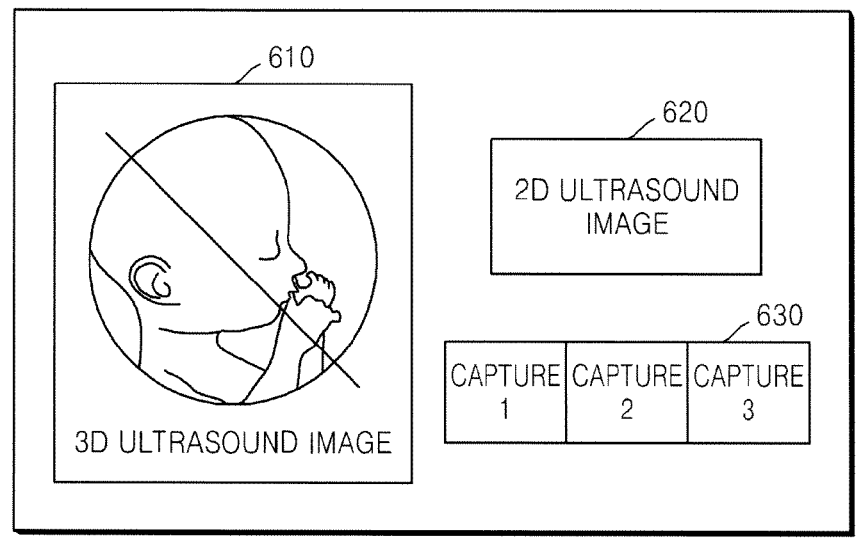
FIG. 6 is a diagram for explaining how an ultrasound image is provided in a 3-dimensional image mode according to an embodiment of the present invention.

FIG. 6 is a diagram for explaining how an ultrasound image is provided in a 3-dimensional image mode according to an embodiment of the present invention.

Referring to FIG. 6, in a 3D image mode according to an embodiment of the present invention, a 3D ultrasound image 610, a 2D ultrasound image 620, and a capture image 630 may be displayed. In the 3D image mode according to an embodiment of the present invention, a 3D ultrasound image is displayed in the largest region.

A cut line or cut surface may be marked on the 3D ultrasound image 610 according to an embodiment of the present invention. The 2D ultrasound image 620 according to an embodiment of the present invention may be an oblique cross-sectional image corresponding to the cut line or the cut surface on the 3D ultrasound image 610. The capture image 630 according to an embodiment of the present invention may include a plurality of 2D ultrasound images which are captured by a user.

The capture image 630 according to an embodiment of the present invention may be sequentially arranged according to time, or may be categorized according to a degree of relationship of images and displayed correspondingly. Alternatively, the capture image 630 may be displayed randomly.

Figure 7:
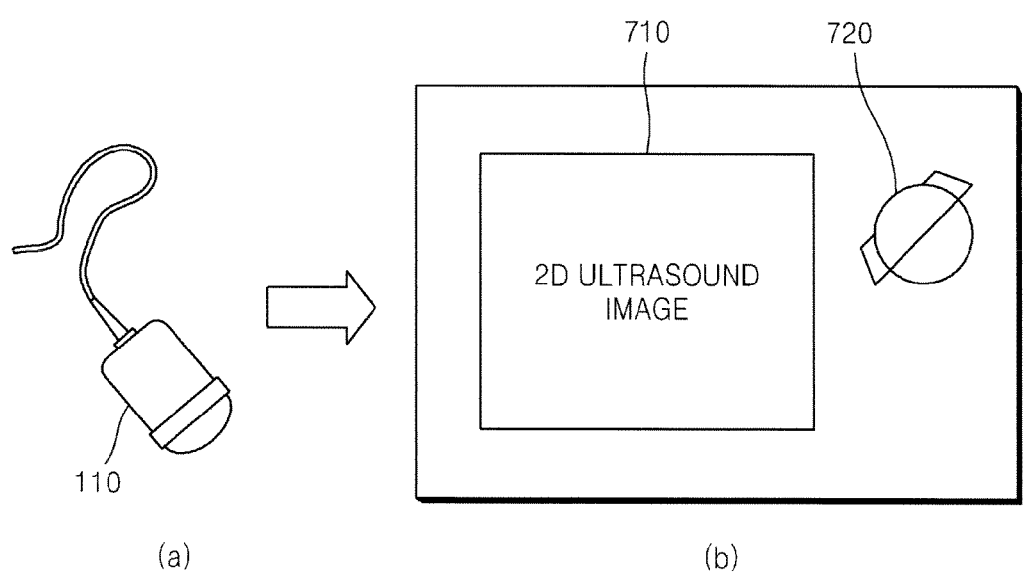
FIG. 7 is a diagram for explaining how an ultrasound image is provided in a 2-dimensional image mode according to an embodiment of the present invention.

FIG. 7 is a diagram for explaining how an ultrasound image is provided in a 2D image mode according to an embodiment of the present invention.

Referring to FIG. 7, in a 2D image mode according to an embodiment of the present invention, the ultrasound apparatus 100 may display a 2D ultrasound image 710 and a 3D ultrasound image 720 on which the location corresponding to the 2D ultrasound image 710 is marked. The 2D ultrasound image 710 in the 2D image mode may be displayed in a wider region than the 2D ultrasound image 620 in the 3D image mode.

According to an embodiment of the present invention, a user may determine the location of the cut line or the cut surface by moving the probe 110 as soon as an ultrasound image is obtained. Accordingly, the location of the probe 110 that corresponds to a 2D ultrasound image on display may be continuously identified. Accordingly, when the user needs to obtain another ultrasound image, the user may easily determine the location of the probe 110.

Embodiments of the present invention include a computer-readable recording medium including program commands for executing operations implemented through various computers. The computer-readable recording medium can store program commands, data files, data structures, or combinations thereof. The program commands recorded in the computer-readable recording medium may be specially designed and configured for the present invention or be known to those of ordinary skill in the field of computer software. Examples of a computer-readable recording medium include magnetic media such as hard disks, floppy disks, and magnetic tapes, optical media such as CD-ROMs and DVDs, magneto-optical media such as floptical disks, or hardware devices such as ROMs, RAMs, and flash memories, which are specially configured to store and execute program commands. Examples of the program commands include a machine language code created by a compiler and a high-level language code executable by a computer using an interpreter and the like.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:
1. A method of providing an ultrasound image, the method comprising:
marking a cut line or a cut surface on a 3-dimensional (3D) ultrasound image of an object which is obtained by using a probe, wherein the cut line and the cut surface are used to view a cross section of the 3D ultrasound image;
detecting motion information about the probe by using a sensor included in the probe;
changing a location of the cut line or the cut surface based on the detected motion information about the probe;

displaying a 2 dimensional (2D) ultrasound image corresponding to the changed location of the cut line or the cut surface;

receiving a mode conversion command for converting a 3D image mode into a 2D image mode through a button included in the probe; and displaying a 2D ultrasound image corresponding to a location of the probe based on the mode conversion command in real time.

2. The method of claim 1, further comprising capturing the 2D ultrasound image corresponding to the changed location of the cut line or the cut surface.

3. The method of claim 1, wherein the displaying of the 2D ultrasound image in real time further comprises:

displaying the 2D ultrasound image corresponding to the location of the probe on a first region; and displaying on a second region a 3D ultrasound image on which a location corresponding to the 2D ultrasound image displayed on the first region is marked.

4. The method of claim 1, wherein the motion information comprises information about at least one selected from a tilting direction, tilting angle, rotational direction, and rotational angle of the probe.

5. The method of claim 1, wherein the sensor comprises at least one selected from a tilt sensor, a gyro sensor, a 3-axis magnetic sensor, and an acceleration sensor.

6. A non-transitory computer readable recording medium having recorded thereon a program for executing the method of claim 1.

7. A ultrasound apparatus comprising:

a probe comprising a sensor for detecting motion information and a button for receiving an input of a mode conversion command for converting a 3D image mode into a 2D image mode;

a display unit for marking a cut line or a cut surface on a 3D ultrasound image of an object which is obtained by using the probe to view a cross section of the 3D ultrasound image;

an image processor for changing a location of the cut line or the cut surface, based on motion information of the probe detected by using the sensor; and a controller for controlling the probe, the display unit, and the image processor.

8. The ultrasound apparatus of claim 7, wherein the display unit displays a 2D ultrasound image corresponding to the changed location of the cut line or the cut surface.

9. The ultrasound apparatus of claim 8, wherein the controller captures the 2D ultrasound image on display.

10. The ultrasound apparatus of claim 8, wherein the controller receives the mode conversion command for converting the 3D image mode into the 2D image mode through the button, and the display unit displays a 2D ultrasound image corresponding to a location of the probe, based on the mode conversion command, in real time.

11. The ultrasound apparatus of claim 10, wherein the display unit displays, in the 2D image mode, the 2D ultrasound image corresponding to the location of the probe on a first region, and a 3D ultrasound image on which a location corresponding to the 2D ultrasound image displayed on the first region is marked on a second region.

12. The ultrasound apparatus of claim 7, wherein the motion information comprises information about at least one selected from a tilting direction, tilting angle, rotational direction, and rotational angle of the probe.

13. The ultrasound apparatus of claim 7, wherein the sensor comprises at least one selected from a tilt sensor, a gyro sensor, a 3-axis magnetic sensor, and an acceleration sensor.

* * * * *